(12) United States Patent
Lingam et al.

(10) Patent No.: US 8,492,568 B2
(45) Date of Patent: Jul. 23, 2013

(54) CHROMANE DERIVATIVES AS TRPV3 MODULATORS

(75) Inventors: V. S. Prasada Rao Lingam, Navi Mumbai (IN); Abraham Thomas, Navi Mumbai (IN); Javed Yusuf Khatik, Thane (IN); Neelima Khairatkar-Joshi, Thane (IN); Vidya Ganapati Kattige, Thane (IN)

(73) Assignee: Glenmark Pharamceuticals S.A., La Chaux-de-Fonds (CH)

( * ) Notice: Subject to any disclaimer, the term of this patent is extended or adjusted under 35 U.S.C. 154(b) by 296 days.

(21) Appl. No.: 12/937,634

(22) PCT Filed: May 19, 2009

(86) PCT No.: PCT/IB2009/005641
§ 371 (c)(1),
(2), (4) Date: Oct. 13, 2010

(87) PCT Pub. No.: WO2010/004379
PCT Pub. Date: Jan. 14, 2010

(65) Prior Publication Data
US 2011/0098316 A1    Apr. 28, 2011

Related U.S. Application Data

(60) Provisional application No. 61/078,603, filed on Jul. 7, 2008.

(30) Foreign Application Priority Data

Jun. 17, 2008  (IN) .......................... 1274/MUM/2008

(51) Int. Cl.
*C07D 311/96* (2006.01)
*C07D 215/38* (2006.01)
*A61K 31/4709* (2006.01)
*A61K 31/352* (2006.01)

(52) U.S. Cl.
USPC ........... 549/345; 546/171; 548/159; 548/195; 514/315; 514/367; 514/370; 514/396

(58) Field of Classification Search
USPC ... 549/345; 514/456, 315, 367, 370; 548/159, 548/195; 546/171
See application file for complete search history.

(56) References Cited

U.S. PATENT DOCUMENTS

| 4,537,962 | A | 8/1985 | Doria et al. |
| 5,418,245 | A | 5/1995 | Spada et al. |
| 6,610,749 | B2 | 8/2003 | Liao et al. |
| 6,734,208 | B2 | 5/2004 | Grainger et al. |
| 6,797,819 | B1 | 9/2004 | Shair et al. |
| 7,576,094 | B2 | 8/2009 | Chu et al. |
| 7,842,703 | B2 | 11/2010 | Gharat et al. |
| 2004/0009537 | A1 | 1/2004 | Roos et al. |
| 2005/0239899 | A1 | 10/2005 | Fecke et al. |
| 2007/0179164 | A1 | 8/2007 | Chong et al. |
| 2007/0219187 | A1 | 9/2007 | Bessis et al. |
| 2008/0096892 | A1 | 4/2008 | Cheng et al. |
| 2008/0131367 | A1 | 6/2008 | Mori et al. |
| 2008/0287428 | A1* | 11/2008 | Uchida et al. .............. 514/230.5 |

FOREIGN PATENT DOCUMENTS

| EP | 1908753 A1 | 4/2008 |
| JP | 07242666 A | 9/1995 |
| WO | 02/04444 A2 | 1/2002 |
| WO | 2008/091021 A1 | 7/2008 |

OTHER PUBLICATIONS

Hu, H.Z. et al., Journal of Cellular Physiology, (2006), 2008, 201-212.
Supplementary European Search Report dated Jul. 24, 2012.

\* cited by examiner

*Primary Examiner* — Bernard Dentz
(74) *Attorney, Agent, or Firm* — Pergament Gilman & Cepeda LLP; Milagros A. Cepeda; Edward D. Pergament

(57) ABSTRACT

The present invention provides chromane derivatives as transient receptor potential vanilloid (TRPV) modulators. In particular, the compounds described herein are useful for treating or preventing diseases, conditions and/or disorders modulated by TRPV3. Also provided herein are processes for preparing compounds described herein, intermediates used in their synthesis, pharmaceutical compositions thereof, and methods for treating or preventing diseases, conditions and/or disorders modulated by TRPV3.

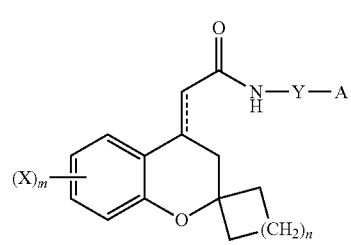

(I)

19 Claims, No Drawings

CHROMANE DERIVATIVES AS TRPV3 MODULATORS

RELATED APPLICATIONS

This application claims the benefit of Indian Provisional Applications Nos. 1274/MUM/2008, filed on Jun. 17, 2008, and U.S. Provisional Applications Nos. 61/078,603, filed on Jul. 7, 2008, all of which are hereby incorporated by reference in their entirety. This is the national phase application with reference to the PCT application number PCT/IB2009/005641 filed on May 19, 2009.

TECHNICAL FIELD

The present patent application relates to chromane derivatives with Transient Receptor Potential Vanilloid 3 (TRPV3) activity.

BACKGROUND

Movement of ions across cellular membranes is carried out by specialized proteins. TRP channels are one large family of non-selective cation channels that function to help regulate ion flux and membrane potential. TRP channels are subdivided into 6 sub-families including the TRPV family. TRPV3 is a member of the TRPV class of TRP channels.

TRPV3 is a calcium permeable nonselective cation channel. In addition to calcium ions, TRPV3 channels are permeable to other cations, for example sodium. Thus, TRPV3 channels modulate membrane potential by modulating the flux of cations such as calcium and sodium ions. TRPV3 receptors are mechanistically distinct from voltage-gated calcium channels. Generally, voltage-gated calcium channels respond to membrane depolarization and open to permit an influx of calcium from the extracellular medium that result in an increase in intracellular calcium levels or concentrations. In contrast, TRP channels which are non-selective, long lasting, produce more prolonged changes in ion concentration and are ligand gated (modulated by chemicals such as 2-aminoethoxydiphenyl borate [2-APB], vanilloids and heat). These mechanistic differences are accompanied by structural differences among voltage-gated and TRP channels. Thus, although many diverse channels act to regulate ion flux and membrane potential in various cell types and in response to numerous stimuli, it is important to recognize the significant structural, functional, and mechanistic differences among different classes of ion channels.

TRPV3 proteins are thermosensitive channels expressed in skin cells (Peier et al. *Science* (2002), 296, 2046-2049) and dorsal root ganglion, trigeminal ganglion, spinal cord and brain (Xu et al. *Nature* (2002), 418, 181-185; Smith et al. *Nature* (2002), 418, 186-188). In a keratinocyte cell line, stimulation of TRPV3 leads to release of inflammatory mediators including interleukin-1. Thus TRPV3 may also play an important role in regulating inflammation and pain that results from the release of inflammatory stimuli. Particular TRPV3 proteins that may be used in screening assays, as described herein, to identity compounds that modulate a function of TRPV3 include, but are not limited to human TRPV3, mouse TRPV3, rat TRPV3 and Drosophila TRPV3. US2004/0009537 (the '537 application) disclosed sequences corresponding to human, mouse, and Drosophila TRPV3. For example, SEQ ID Nos 106 and 107 of the '537 application correspond to the human nucleic acid and amino acid sequences, respectively. SEQ ID Nos 108 and 109 of the '537 application correspond to the mouse nucleic acid and amino acid sequences, respectively.

TRPV3 function has been basically implicated in the reception and transduction of pain. Accordingly, it would be desirable to identify and make compounds that can modulate one or more functions of TRPV3.

WO 2007/056124, WO 2008/140750 and WO 2008/033564 disclose TRPV3 modulators, in particular antagonists, for treatment of various diseases mediated TRPV3.

In efforts to discover better analgesics, there still exists a need for therapeutic treatment of diseases, conditions and/or disorders modulated by TRPV3.

SUMMARY

The present patent application relates to compounds of the formula (I):

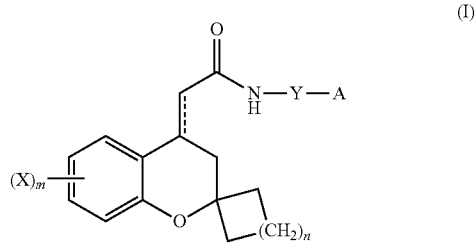

wherein dotted ( ... ) line is an optional bond;
A is substituted or unsubstituted cycloalkyl, aryl, heteroaryl, or heterocyclic group;
Y is —$(CHR^1)_r$ wherein $R^1$ is hydrogen, halogen, or substituted or unsubstituted alkyl;
X is hydrogen, nitro, cyano, halogen, substituted or unsubstituted alkyl, —$OR^2$, —$NR^3R^4$, —$C(O)$—$R^3$, —$C(O)O$—$R^3$, —$C(O)NR^3R^4$, —$S(O)_pNR^3R^4$, or —$S(O)_pR^3$;
at each occurrence $R^3$ and $R^4$, which may be same or different, are independently selected from hydrogen, —$OR^2$, substituted or unsubstituted alkyl, alkenyl, cycloalkyl cycloalkylalkyl, cycloalkenyl, aryl, arylalkyl, heteroaryl, heteroarylalkyl, heterocyclic group, or heterocyclylalkyl;
at each occurrence $R^2$ is selected from the group consisting of hydrogen, substituted or unsubstituted alkyl, alkenyl, cycloalkyl, aryl, heteroaryl, heterocyclic group, cycloalkylalkyl, arylalkyl, heteroarylalkyl, or heterocyclylalkyl;
'm' is an integer ranging from 0 to 2, both inclusive;
'n' is an integer ranging from 0 to 2, both inclusive;
'p' is an integer ranging from 0 to 2, both inclusive; and
'r' is an integer ranging from 0 to 2, both inclusive.

It should be understood that the formula (I) structurally encompasses all stereoisomers, including enantiomers and diastereomers, and pharmaceutically acceptable salts that may be contemplated from the chemical structure of the genus described herein.

According to one embodiment, specifically provided are compounds of formula (I), in which 'A' is substituted or unsubstituted aryl. In this embodiment, preferably, 'A' is substituted or unsubstituted phenyl or napthyl, wherein the substituent(s) are independently selected from halogen (for e.g., fluorine or chlorine), alkoxy (for e.g., methoxy), or cycloalkoxy (for e.g., cyclopentyloxy).

According to another embodiment, specifically provided are compounds of formula (I), in which 'A' is substituted or unsubstituted heteroaryl. In this embodiment, preferably, 'A' is substituted or unsubstituted thiazole, benzothiazole, quinoline or dibenzo[b,d]furan, wherein substituent(s) are independently selected from halogen, alkyl (for e.g., methyl), alkoxy (for e.g., methoxy), cycloalkoxy, or halophenyl (for e.g., bromophenyl).

According to another embodiment, specifically provided are compounds of formula (I), in which 'Y' is $CH_2$, $CH(CH_3)$ or a bond.

According to another embodiment, specifically provided are compounds of formula (I), in which dotted ( . . . ) line is a single bond or absent.

According to another embodiment, specifically provided are compounds of formula (I), in which X is halogen (for e.g., fluorine or chlorine) or alkoxy (for e.g., methoxy); and 'm' is 1.

According to another embodiment, specifically provided are compounds of formula (I), in which 'n' is 1.

Below are the representative compounds, which are illustrative in nature only and are not intended to limit to the scope of the invention.

2-(6-Chloro-3,4-dihydrospiro[chromene-2,1'-cyclobutan]-4-yl)-N-(2-methoxyphenyl)acetamide, 2-(6-Chloro-3,4-dihydrospiro[chromene-2,1'-cyclobutan]-4-yl)-N-(2-cyclopentyloxy-3-methoxy benzyl)acetamide, 2-(6-Chloro-3,4-dihydrospiro[chromene-2,1'-cyclobutan]-4-yl)-N-1-(4-methoxynaphthylmethyl)acetamide, 2-(6-Chloro-3,4-dihydrospiro[chromene-2,1'-cyclobutan]-4-yl)-N-[(4-methoxydibenzo[b,d]furan-1-yl)methyl]acetamide, 2-(6-Chloro-3,4-dihydrospiro[chromene-2,1'-cyclobutan]-4-yl)-N-[(1S)-1-phenylethyl]acetamide, (2E)-2-(6-Chloro-3,4-dihydrospiro[chromene-2,1'-cyclobutan]-4-ylidene)-N-[2-(cyclopentyloxy)phenyl]acetamide, N-(2-Cyclopentyloxyphenyl)-2-(6-fluoro-3,4-dihydrospiro[chromene-2,1'-cyclobutan]-4-yl)acetamide, N-(2,6-Difluorobenzyl)-2-(6-fluoro-3,4-dihydrospiro[chromene-2,1'-cyclobutan]-4-yl)acetamide, 2-(6-Fluoro-3,4-dihydrospiro[chromene-2,1'-cyclobutan]-4-yl)-N-quinolin-6-ylacetamide, N-[4-(4-Bromophenyl)-1,3-thiazol-2-yl]-2-(6-fluoro-3,4-dihydrospiro[chromene-2,1'-cyclobutan]-4-yl)acetamide, 2-(6-Methoxy-3,4-dihydrospiro[chromene-2,1'-cyclobutan]-4-yl)-N-1-naphthylacetamide, 2-(6-Methoxy-3,4-dihydrospiro[chromene-2,1'-cyclobutan]-4-yl)-N-1,3-thiazol-2-ylacetamide and 2-(6-Methoxy-3,4-dihydrospiro[chromene-2,1'-cyclobutan]-4-yl)-N-(6-Methyl-1,3-benzothiazol-2-yl)acetamide or an analog, tautomer, regiomer, geometrical isomers, stereoisomer, enantiomer, diastereomer or pharmaceutically acceptable salt of compounds 1 to 13 are also contemplated.

According to another embodiment, specifically provided are compounds of Formula I, or a salt thereof, that inhibits a TRPV3 function with an $IC_{50}$ value of less than 10,000 nM. In other embodiments, specifically provided are compounds of Formula I, or a salt thereof, that inhibits a TRPV3 function with an $IC_{50}$ value of less than 1000 nM.

Also provided herein are processes for preparing compounds described herein.

DETAILED DESCRIPTION

The present patent application provides chromane derivatives, which may be used as TRPV3 modulators, and processes for the synthesis of these compounds. Pharmaceutically acceptable salts, enantiomers, and diastereomers of compounds described herein are separately and individually contemplated. Pharmaceutical compositions containing the described compounds together with pharmaceutically acceptable carriers, excipients or diluents, which can be used for the treatment of diseases, condition and/or disorders mediated by TRPV3 are separately contemplated.

The invention is defined by the claims and not limited by the description provided herein below. The terms used in the appended claims are defined herein in this glossary section, with the proviso that the claim terms may be used in a different manner if so defined by express recitation.

The terms "halogen" or "halo" includes fluorine, chlorine, bromine, or iodine.

The term "alkyl" refers to hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (iso-propyl), n-butyl, n-pentyl, and 1,1-dimethylethyl (tert-butyl). The term "$C_{1-6}$ alkyl" refers to an alkyl chain having 1 to 6 carbon atoms. Unless set forth or recited to the contrary, all alkyl groups described or claimed herein may be straight chain or branched, substituted or unsubstituted.

The term "alkenyl" refers to an hydrocarbon chain containing from 2 to 10 carbon atoms and including at least one carbon-carbon double bond. Non-limiting examples of alkenyl groups include ethenyl, 1-propenyl, 2-propenyl (allyl), iso-propenyl, 2-methyl-1-propenyl, 1-butenyl, and 2-butenyl. Unless set forth or recited to the contrary, all alkenyl groups described or claimed herein may be straight chain or branched, substituted or unsubstituted.

The term "alkynyl" refers to a hydrocarbyl radical having at least one carbon-carbon triple bond, and having 2 to about 12 carbon atoms (with radicals having 2 to about 10 carbon atoms being preferred). Non-limiting examples of alkynyl groups include ethynyl, propynyl, and butynyl. Unless set forth or recited to the contrary, all alkynyl groups described or claimed herein may be straight chain or branched, substituted or unsubstituted.

The term "alkoxy" denotes an alkyl group attached via an oxygen linkage to the rest of the molecule. Representative examples of such groups are —$OCH_3$ and —$OC_2H_5$. Unless set forth or recited to the contrary, all alkoxy groups described or claimed herein may be straight chain or branched, substituted or unsubstituted.

The term "cycloalkyl" denotes a non-aromatic mono or multicyclic ring system of 3 to about 12 carbon atoms, such as cyclopropyl, cyclobutyl, cyclopentyl, and cyclohexyl. Examples of multicyclic cycloalkyl groups include, but are not limited to, perhydronaphthyl, adamantyl and norbornyl groups, bridged cyclic groups or spirobicyclic groups, e.g., sprio(4,4)non-2-yl. Unless set forth or recited to the contrary, all cycloalkyl groups described or claimed herein may be substituted or unsubstituted.

The term "cycloalkylalkyl" refers to a cyclic ring-containing radical having 3 to about 8 carbon atoms directly attached to an alkyl group. The cycloalkylalkyl group may be attached to the main structure at any carbon atom in the alkyl group that results in the creation of a stable structure. Non-limiting examples of such groups include cyclopropylmethyl, cyclobutylethyl, and cyclopentylethyl. Unless set forth or recited to the contrary, all cycloalkylalkyl groups described or claimed herein may be substituted or unsubstituted.

The term "cycloalkenyl" refers to a cyclic ring-containing radical having 3 to about 8 carbon atoms with at least one carbon-carbon double bond, such as cyclopropenyl, cyclobutenyl, and cyclopentenyl. Unless set forth or recited to the contrary, all cycloalkenyl groups described or claimed herein may be substituted or unsubstituted.

The term "aryl" refers to an aromatic radical having 6 to 14 carbon atoms, including monocyclic, bicyclic and tricyclic aromatic systems, such as phenyl, naphthyl, tetrahydronaphthyl, indanyl, and biphenyl. Unless set forth or recited to the contrary, all aryl groups described or claimed herein may be substituted or unsubstituted.

The term "arylalkyl" refers to an aryl group as defined above directly bonded to an alkyl group as defined above, e.g., —$CH_2C_6H_5$ and —$C_2H_4C_6H_5$.

The term "heterocyclyl" and "heterocyclic ring" "heterocyclic group" refers to a stable 3- to 15-membered ring radical which consists of carbon atoms and from one to five heteroatoms selected from nitrogen, phosphorus, oxygen and sulfur. For purposes of this invention, the heterocyclic ring radical may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heterocyclic or heteroaryl). Examples of such heterocyclic ring radicals include, but are not limited to, azetidinyl, acridinyl, benzodioxolyl, benzodioxanyl, benzofuranyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazolyl, imidazolyl, tetrahydroisoquinolinyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxazolidinyl, triazolyl, indanyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, furyl, tetrahydrofuranyl, tetrahydropyranyl, thienyl, benzothienyl, thiamorpholinyl, thiamorpholinyl sulfoxide, thiamorpholinyl sulfone, dioxaphospholanyl, oxadiazolyl, chromanyl, and isochromanyl. The heterocyclic ring radical may be attached to the main structure at any heteroatom or carbon atom that results in the creation of a stable structure. Unless set forth or recited to the contrary, all heterocyclyl groups described or claimed herein may be substituted or unsubstituted, including those included in more complex substructures.

The term "heterocyclylalkyl" refers to a heterocyclic ring radical directly bonded to an alkyl group. The heterocyclylalkyl radical may be attached to the main structure at any carbon atom in the alkyl group that results in the creation of a stable structure.

The term "heteroaryl" refers to an aromatic heterocyclic ring radical. The heteroaryl ring radical may be attached to the main structure at any heteroatom or carbon atom that results in the creation of a stable structure. Unless set forth or recited to the contrary, all heteroaryl groups described or claimed herein may be substituted or unsubstituted, including those included in more complex substructures.

The term "heteroarylalkyl" refers to a heteroaryl ring radical directly bonded to an alkyl group. The heteroarylalkyl radical may be attached to the main structure at any carbon atom in the alkyl group that results in the creation of a stable structure.

Unless otherwise specified, the term "substituted" as used herein refers to a group or moiety having one or more of the substituents attached to the structural skeleton of the group or moiety, including, but not limited to such substituents as hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenylalkyl, substituted or unsubstituted cycloalkenyl, substituted or unsubstituted amino, substituted or unsubstituted aryl, substituted or unsubstituted heteroaryl, substituted or unsubstituted heterocyclylalkyl ring, substituted or unsubstituted heteroarylalkyl, substituted or unsubstituted heterocyclic ring, substituted or unsubstituted guanidine, —$COOR^x$, —$C(O)R^x$, —$C(S)R^x$, —$C(O)NR^xR^y$, —$C(O)ONR^xR^y$, —$NR^xCONR^yR^z$, —$N(R^x)SOR^y$, —$N(R^x)SO_2R^y$, —$(=N-N(R^x)R^y)$, —$NR^xC(O)OR^y$, —$NR^xR^y$, —$NR^xC(O)R^y$, —$NR^xC(S)R^y$, —$NR^xC(S)NR^yR^z$, —$SONR^xR^y$, —$SO_2NR^xR^y$, —$OR^x$, —$OR^xC(O)NR^yR^z$, —$OR^xC(O)OR^y$, —$OC(O)R^x$, —$OC(O)NR^xR^y$, —$R^xNR^yC(O)R^z$, —$R^xOR^y$, —$R^xC(O)OR^y$, —$R^xC(O)NR^yR^z$, —$R^xC(O)R^y$, —$R^xOC(O)R^y$, —$SR^x$, —$SOR^x$, —$SO_2R^x$, and —$ONO_2$, wherein $R^x$, $R^y$ and $R^z$ are independently selected from hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocyclylalkyl ring, substituted or unsubstituted heteroarylalkyl, or substituted or unsubstituted heterocyclic ring.

The term "treating" or "treatment" of a state, disorder or condition includes: (a) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition; (b) inhibiting the state, disorder or condition, i.e., arresting or reducing the development of the disease or at least one clinical or subclinical symptom thereof; or (c) relieving the disease, i.e., causing regression of the state, disorder or condition or at least one of its clinical or subclinical symptoms.

The term "subject" includes mammals (especially humans) and other animals, such as domestic animals (e.g., household pets including cats and dogs) and non-domestic animals (such as wildlife).

A "therapeutically effective amount" means the amount of a compound that, when administered to a subject for treating a state, disorder or condition, is sufficient to cause the effect in the subject which is the purpose of the administration. The "therapeutically effective amount" will vary depending on the compound, the disease and its severity and the age, weight, physical condition and responsiveness of the subject to be treated.

The compound described in the present patent application may form salts. Non-limiting examples of pharmaceutically acceptable salts forming part of this patent application include salts derived from inorganic bases, salts of organic bases, salts of chiral bases, salts of natural amino acids and salts of non-natural amino acids. With respect to the overall compounds described by the Formula (I), the present patent application extends to these stereoisomeric forms and to mixtures thereof. To the extent prior art teaches synthesis or separation of particular stereoisomers, the different stereoisomeric forms of the present patent application may be separated from one another by the method known in the art, or a given isomer may be obtained by stereospecific or asymmetric synthesis. Tautomeric forms and mixtures of compounds described herein are also contemplated.

Pharmaceutical Compositions

The pharmaceutical composition provided in the present invention includes at least one compound described herein and at least one pharmaceutically acceptable excipient (such as a pharmaceutically acceptable carrier or diluent). Preferably, the contemplated pharmaceutical compositions include the compound(s) described herein in an amount sufficient to inhibit TRPV3 receptor in a subject.

The subjects contemplated include, for example, a living cell and a mammal, including human. The compound of the present invention may be associated with a pharmaceutically acceptable excipient (such as a carrier or a diluent) or be diluted by a carrier, or enclosed within a carrier which can be in the form of a capsule, sachet, paper or other container.

Examples of suitable carriers include, but are not limited to, water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone.

The carrier or diluent may include a sustained release material, such as glyceryl monostearate or glyceryl distearate, alone or mixed with a wax.

The pharmaceutical composition may also include one or more pharmaceutically acceptable auxiliary agents, wetting agents, emulsifying agents, suspending agents, preserving agents, salts for influencing osmotic pressure, buffers, sweetening agents, flavoring agents, colorants, or any combination of the foregoing. The pharmaceutical composition of the invention may be formulated so as to provide quick, sustained, or delayed release of the active ingredient after administration to the subject by employing procedures known in the art.

The pharmaceutical compositions described herein may be prepared by conventional techniques known in the art. For example, the active compound can be mixed with a carrier, or diluted by a carrier, or enclosed within a carrier, which may be in the form of an ampoule, capsule, sachet, paper, or other container. When the carrier serves as a diluent, it may be a solid, semi-solid, or liquid material that acts as a vehicle, excipient, or medium for the active compound. The active compound can be adsorbed on a granular solid container, for example, in a sachet.

The pharmaceutical compositions may be in conventional forms, for example, capsules, tablets, aerosols, solutions, suspensions or products for topical application.

The route of administration may be any route which effectively transports the active compound of the invention to the appropriate or desired site of action. Suitable routes of administration include, but are not limited to, oral, nasal, pulmonary, buccal, subdermal, intradermal, transdermal, parenteral, rectal, depot, subcutaneous, intravenous, intraurethral, intramuscular, intranasal, ophthalmic (such as with an ophthalmic solution) or topical (such as with a topical ointment).

Solid oral formulations include, but are not limited to, tablets, capsules (soft or hard gelatin), dragees (containing the active ingredient in powder or pellet form), troches and lozenges. Tablets, dragees, or capsules having talc and/or a carbohydrate carrier or binder or the like are particularly suitable for oral application. Liquid formulations include, but are not limited to, syrups, emulsions, soft gelatin and sterile injectable liquids, such as aqueous or non-aqueous liquid suspensions or solutions. For parenteral application, particularly suitable are injectable solutions or suspensions. Preferably aqueous solutions with the active compound dissolved in polyhydroxylated castor oil.

Suitable doses of the compounds for use in treating the diseases and disorders described herein can be determined by those skilled in the relevant art. Therapeutic doses are generally identified through a dose ranging study in humans based on preliminary evidence derived from the animal studies. Doses must be sufficient to result in a desired therapeutic benefit without causing unwanted side effects. For example, the daily dosage of the TRPV3 modulator can range from about 0.1 to about 30.0 mg/kg. Mode of administration, dosage forms, suitable pharmaceutical excipients, diluents or carriers can also be well used and adjusted by those skilled in the art. All changes and modifications are envisioned within the scope of the present invention.

Methods of Treatment

The present invention provides compounds and pharmaceutical formulations thereof that are useful in the treatment of diseases, conditions and/or disorders modulated by TRPV3. The present patent application further provides a method of treating a disease, condition and/or disorder modulated by TRPV3 in a subject in need thereof by administering to the subject a therapeutically effective amount of a compound or a pharmaceutical composition of the present invention.

Diseases, conditions, and/or disorders that are modulated by TRPV3 are believed to include, but are not limited to pain, nociceptive pain, dental pain, cardiac pain arising from an ischemic myocardium, pain due to migraine, acute pain, chronic pain, neuropathic pain, post-operative pain, pain due to neuralgia (e.g., post-herpetic neuralgia or trigeminal neuralgia), pain due to diabetic neuropathy, dental pain and cancer pain, inflammatory pain conditions (e.g. arthritis and osteoarthritis), arthralgia, neuropathies, neurodegeneration, retinopathy, neurotic skin disorder, stroke, urinary bladder hypersensitiveness, urinary incontinence, vulvodynia, gastrointestinal disorders such as irritable bowel syndrome, gastro-esophageal reflux disease, enteritis, ileitis, stomach-duodenal ulcer, inflammatory bowel disease, Crohn's disease, celiac disease, an inflammatory disease such as pancreatitis, a respiratory disorder such as allergic and non-allergic rhinitis, asthma or chronic obstructive pulmonary disease, irritation of skin, eye or mucous membrane, dermatitis, pruritic conditions such as uremic pruritus, fervescence, muscle spasms, emesis, dyskinesias, depression, Huntington's disease, memory deficits, restricted brain function, amyotrophic lateral sclerosis (ALS), dementia, arthritis, osteoarthritis, diabetes, obesity, urticaria, actinic keratosis, keratoctanthoma, alopecia, Meniere's disease, tinnitus, hyperacusis, anxiety disorders and benign prostate hyperplasia. Additional diseases, conditions and/or disorders modulated by TRPV3 is illustrated, for example in WO2007/056124; Wissenbach, U. et al, *Biology of the cell* (2004), 96, 47-54; Nilius, B. et al., *Physiol Rev* (2007), 87, 165-217; Okuhara, D. Y. et al, *Expert*

Opinion on Therapeutic Targets (2007), 11, 391-401; Hu, H. Z. et al, Journal of Cellular Physiology, (2006), 208, 201-212 and references cited therein, all of which are incorporated herein by reference in their entirety and for the purpose stated.

General Methods of Preparation

The compounds described herein, including compounds of general formula (I) and specific examples are prepared using techniques known to one of ordinary skill in the art. The compounds described herein are prepared through the reaction sequences as depicted in Scheme-1. All possible stereoisomers are also envisioned within the scope of this invention.

The starting materials for the below reaction schemes are commercially available or can be prepared according to methods known to one skilled in the art or by methods disclosed herein. In general, the compounds according to the present invention may be prepared through the reaction schemes as follows, wherein all symbols are as defined above.

Compounds of formula (I) can be prepared according to Synthetic scheme 1. Thus, 2-hydroxy acetophenone of the formula (1) is condensed with a cyclic ketone of the formula (2) in the presence of a base such as pyrrolidine or piperidine in alcoholic solvents gives spirocyclic ketone of formula (3) which on reaction with trialkyl phosphonoacetate of formula (4) under Wittig reaction conditions where R is alkyl, gives a acrylic ester of the formula (5) where R is alkyl. Hydrolysis of compound of formula (5) followed by catalytic hydrogenation (optional) gives compound of formula (6). The compounds of the general formula (I) is prepared by coupling carboxylic acid of formula (6) with an appropriate amine of the formula (7) in the presence of a suitable coupling agent. Alternatively, acid chloride of intermediate (6) can be coupled with the amine of the formula (7) in the presence of a suitable base to give compound of the general formula (I).

implemented as disclosed by variously altering the following examples, substituents, reagents, or conditions.

Intermediates

Intermediate 1

(6-Chloro-3,4-dihydrospiro[chromene-2,1'-cyclobutan]-4-yl)acetic acid

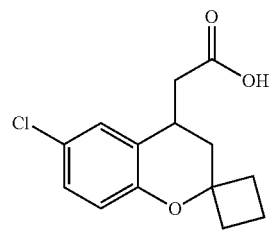 [SMILES: O=C(O)CC1CC2(CCC2)Oc2ccc(Cl)cc21]

Step 1: 6-Chlorospiro[chromene-2,1'-cyclobutan]-4(3H)-one

To a stirred solution of 5'-chloro-2'-hydroxy acetophenone (5.0 g, 29.308 mmol) in methanol (50 ml) was added pyrrolidine (4.16 g, 58.616 mmol) followed by cyclobutanone (4.1 g, 58.616 mmol) at room temperature. The reaction mixture was heated to reflux under nitrogen for 14 h. The solvent was evaporated under reduced pressure and the residue obtained Scheme 1

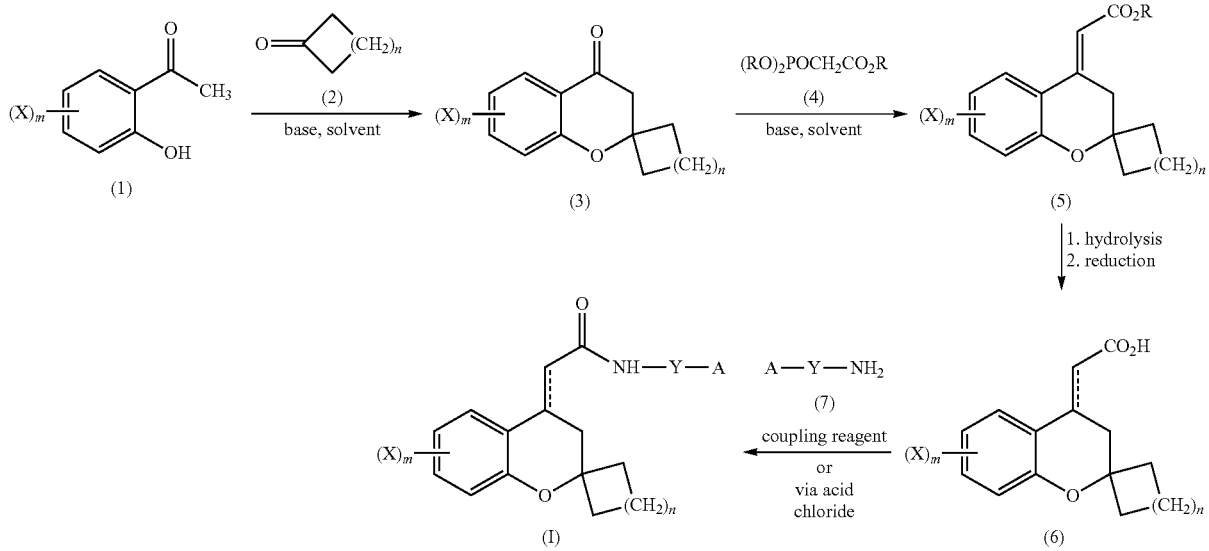

EXPERIMENTAL

The present invention is further illustrated by the following examples, which are not to be construed in any way as imposing limitations upon the scope of this disclosure, but rather are intended to be illustrative only. Thus, the skilled artisan will appreciate how the experiments and Examples may be further was diluted with water (100 ml) and the mixture was acidified to pH 4.0. The mixture was extracted with chloroform (3×100 ml). The combined organic extracts were washed with water (100 ml), brine (50 ml) and dried over anhydrous sodium sulfate. The residue obtained after evaporation of the solvent was purified by silica gel column chromatography using 15% ethyl acetate in petroleum ether to give 6.3 g of the product as a white solid; $^1$H NMR (300 MHz, CDCl$_3$) δ 1.69-1.88 (m, 5H), 1.96-2.04 (m, 1H), 2.88 (s, 2H), 6.91 (d, J=9.0 Hz, 1H), 7.38 (d, J=6.6 Hz, 1H), 7.76 (s, 1H).

Step 2: Ethyl (2E)-(6-chlorospiro[chromene-2,1'-cyclobutan]-4(3H)-ylidene)acetate Triethyl phosphonoacetate (4.03 g, 17.897 mmol) was added over 15 min to a stirred and cooled mixture of sodium hydride (431 mg, 17.897 mmol) in anhydrous tetrahydrofuran (25 ml). The reaction mixture was stirred for 30 min and then added 6-Chlorospiro[chromene-2,1'-cyclobutan]-4(3H)-one (2 g, 8.948 mmol) in anhydrous tetrahydrofuran. The reaction mixture was stirred at the same temperature under nitrogen for 24 h. The reaction mixture was diluted with methanol and water and the product was extracted into ethyl acetate (3×100 ml). The organic layer was washed with water (100 ml), brine, dried ($Na_2SO_4$) and concentrated to give 3.54 g of the crude product which was used as such for the next step.

Step 3: (2E)-(6-Chlorospiro[chromene-2,1'-cyclobutan]-4(3H)-ylidene)acetic acid To a stirred solution of ethyl (2E)-(6-chlorospiro[chromene-2,1'-cyclobutan]-4(3H)-ylidene)acetate (3 g, 10.22 mmol) in ethanol (30 ml) was added 1N sodium hydroxide solution (30 ml) at room temperature. The reaction mixture was stirred at room temperature for 2 h. The residue obtained after the evaporation of the solvent under reduced pressure was acidified with 1N HCl. The desired product was extracted into ethyl acetate (3×50 ml), washed with water (100 ml), brine, dried ($Na_2SO_4$) and concentrated to give 2.6 g of the product as a white solid; $^1$H NMR (300 MHz, $CDCl_3$) δ 1.68-1.78 (m, 5H), 1.86-1.96 (m, 1H), 3.96 (s, 2H), 6.36 (s, 1H), 6.80 (d, J=8.1 Hz, 1H), 7.22 (d, J=9.3 Hz, 1H), 7.51 (s, 1H).

Step 4: (6-Chloro-3,4-dihydrospiro[chromene-2,1'-cyclobutan]-4-yl)acetic acid To a stirred solution of (2E)-(6-chlorospiro[chromene-2,1'-cyclobutan]-4(3H)-ylidene)acetic acid (2.5 g, 9.444 mmol) in ethyl acetate (25 ml) was added 10% Pd/C (50 mg) at room temperature. The reaction mixture was stirred for 12 h at 40 psi hydrogen pressure in Paar hydrogenation apparatus. The reaction mixture was filtered through a celite bed, the filtrate was dried ($Na_2SO_4$) and concentrated to give 2.45 g of the product as a white solid; $^1$H NMR (300 MHz, $CDCl_3$) δ 1.68-1.78 (m, 5H), 1.86-1.96 (m, 1H), 2.09-2.21 (m, 2H), 2.29-2.38 (m, 1H), 2.99 (d, J=13.2 Hz, 1H), 3.44 (br s, 1H), 6.73 (d, J=8.1 Hz, 1H), 7.04 (d, J=9.3 Hz, 1H).

Intermediate 2

6-Fluoro-3,4-dihydrospiro[chromene-2,1'-cyclobutan]-4-yl)acetic acid

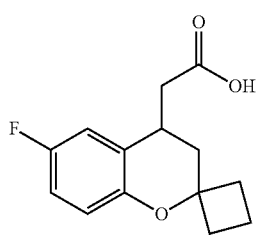 [SMILES: O=C(O)CC1CC2(CCC2)Oc2ccc(F)cc21]

The title compound was prepared in 4 steps from 5'-fluoro-2'-hydroxyacetophenone and cyclobutanone by similar procedure as described in Intermediate 1 to give a white solid; $^1$H NMR (300 MHz, $CDCl_3$) δ 1.66-1.74 (m, 2H), 1.88-1.95 (m, 1H), 2.05-2.14 (m, 3H), 2.26-2.34 (m, 1H), 2.37-2.44 (m, 1H), 2.48-2.56 (m, 1H), 2.96 (dd, J=4.2, 15.6 Hz, 1H), 3.35 (br s, 1H), 6.74-6.82 (m, 3H).

Intermediate 3

(6-Methoxy-3,4-dihydrospiro[chromene-2,1'-cyclobutan]-4-yl)acetic acid

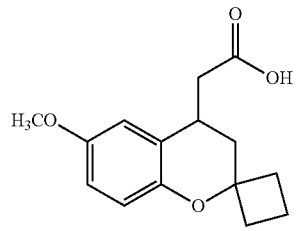 [SMILES: COc1ccc2c(c1)C(CC(=O)O)CC1(CCC1)O2]

Step 1: 6-Hydroxyspiro[chromene-2,1'-cyclobutan]-4-(3H)-one

The title compound was prepared from 2',5'-dihydroxyacetophenone (10 g, 65.724 mmol) and cyclobutanone (13.29 ml, 131.44 mmol), in the presence of pyrrolidine (10.79 ml) by similar procedure as described in Step 1 of Intermediate 1 to give 10 g of the product; $^1$H NMR (300 MHz, $CDCl_3$) δ 1.63-1.73 (m, 2H), 1.84-1.95 (m, 2H), 2.05-2.15 (m, 2H), 2.23-2.33 (m, 2H), 6.85 (d, J=8.7 Hz, 1H), 7.06 (d, J=9.0 Hz, 1H), 7.33 (s, 1H).

Step 2: 6-Methoxyspiro[chromene-2,1'-cyclobutan]-4(3H)-one

To the stirred solution of 6-hydroxyspiro[chromene-2,1'-cyclobutan]-4-(3H)-one (8 g, 39.215 mmol) in dry dimethylformamide (150 ml), potassium carbonate (16.28 g, 117.64 mmol) and methyl iodide (4.88 ml, 78.431 mmol) were added and the reaction mixture was stirred at room temperature under nitrogen atmosphere for 2 h. After the completion of the reaction, the reaction mixture was diluted with water (100 ml), extracted with ethyl acetate (3×300 ml), the combined organic layers washed with water (3×100 ml), brine (60 ml), dried ($Na_2SO_4$), filtered and concentrated to yield 8.13 g of the product; $^1$H NMR (300 MHz, $CDCl_3$) δ 1.67-1.77 (m, 1H), 1.85-1.97 (m, 1H), 2.11-2.18 (m, 2H), 2.23-2.34 (m, 2H), 2.87 (s, 2H), 3.77 (s, 3H), 6.88 (d, J=9.6 Hz, 1H), 7.06 (d, J=8.7 Hz, 1H), 7.25 (s, 1H).

Step 3

The final compound was prepared from 6-Methoxyspiro[chromene-2,1'-cyclobutan]-4(3H)-one by similar procedure as described in Steps 2-4 of Intermediate 1; $^1$H NMR (300 MHz, DMSO-d$_6$) δ 1.53-1.65 (m, 2H), 1.78 (br s, 1H), 1.96-2.05 (m, 3H), 2.18-2.23 (m, 2H), 2.30-2.39 (m, 1H), 2.93 (d, J=15.9 Hz, 1H), 3.18 (br s, 1H), 3.64 (s, 3H), 6.64 (s, 2H), 6.75 (s, 1H).

Intermediate 4

1-[2-(Cyclopentyloxy)-3-methoxyphenyl]methylamine hydrochloride

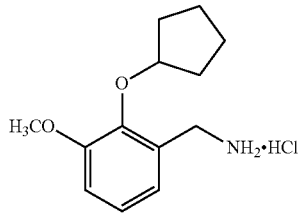

Step 1: 2-(Cyclopentyloxy)-3-methoxybenzaldehyde oxime

To the stirred solution of 2-(cyclopentyloxy)-3-methoxybenzaldehyde (3 g, 13.636 mmol) in ethanol was added hydroxylamine hydrochloride (1.758 g, 27.277 mmol) and aqueous solution of sodium hydroxide (18 ml, 34.091 mmol). The reaction mixture was refluxed for 6 h under nitrogen atmosphere. The solvent was evaporated under reduced pressure and the reaction mixture diluted with water. The product was extracted using chloroform (3×200 ml), combined organic layers washed with water (3×100 ml), brine (50 ml), dried (Na$_2$SO$_4$), filtered and concentrated under vacuum to yield 3.12 g of the product. $^1$H NMR (300 MHz, CDCl$_3$) δ 1.58-1.64 (m, 4H), 1.66-1.72 (m, 4H), 3.84 (s, 3H), 4.86 (br s, 1H), 6.89 (d, J=8.1 Hz, 1H), 6.99 (t, J=7.8 Hz, 1H), 7.31 (d, J=7.8 Hz, 1H), 8.43 (s, 1H).

Step 2: 1-[2-(cyclopentyloxy)-3-methoxyphenyl]methanamine hydrochloride

To a stirred solution of 2-(cyclopentyloxy)-3-methoxybenzaldehyde oxime (3 g, 12.448 mmol) in methanol (10 ml) was added catalytic amount of Raney nickel (0.30 g) at room temperature. The reaction mixture was stirred for 3 h at 50 psi hydrogen pressure in Paar hydrogenation apparatus. The reaction mixture was filtered through celite bed, dried (Na$_2$SO$_4$), filtered and concentrated to get the crude product. The crude product was then dissolved in ethyl acetate, to which hydrochloric acid in ethyl acetate was added dropwise at 10° C. and stirred for 20 min and then filtered and dried to yield 2.86 g of the product, $^1$H NMR (300 MHz, DMSO-d$_6$) δ 1.57-1.63 (m, 4H), 1.65-1.72 (m, 4H), 3.81 (s, 3H), 3.94 (s, 2H), 4.90 (br s, 1H), 7.08 (s, 3H), 8.39 (br s, 3H).

Intermediate 5

1-(4-methoxy-1-naphthyl)methylamine hydrochloride

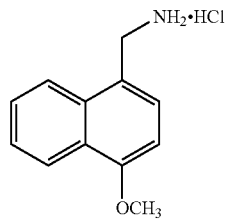

The title compound was prepared in 2 steps from 4-methoxy-1-naphthaldehyde (1 g, 5.376 mmol) by similar procedure as described in Intermediate 4 to give 1.27 g of the product as the hydrochloride salt; $^1$H NMR (300 MHz, CDCl$_3$) δ 3.85 (s, 3H), 4.26 (s, 2H), 6.68 (d, J=7.2 Hz, 1H), 7.40 (br s, 2H), 7.53 (d, J=7.8 Hz, 1H), 7.64 (d, J=7.5 Hz, 1H), 8.19 (d, J=6.6 Hz, 1H).

Intermediate 6

1-(4-methoxydibenzo[b,d]furan-1-yl)methylamine hydrochloride

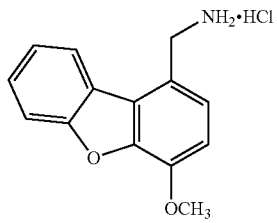

The title compound was prepared in 2 steps from 4-methoxy-dibenzo[b,d]furan-1-carbaldehyde (3 g, 13.274 mmol) by similar procedure as described in Intermediate 4 to give 2.97 g of the product as the hydrochloride salt; $^1$H NMR (300 MHz, CDCl$_3$) δ 4.07 (s, 3H), 4.63 (s, 2H), 7.16 (d, J=8.1 Hz, 1H), 7.36 (d, J=7.8 Hz, 1H), 7.44 (t, J=6.6 Hz, 1H), 7.56 (t, J=7.5 Hz, 1H), 7.66 (d, J=7.5 Hz, 1H), 8.22 (d, J=7.8 Hz, 1H).

EXAMPLES

General procedure for the preparations of 3,4-dihydrospiro[chromene-2,1'-cyclobutan]-4-yl)-N-(2-methoxyphenyl)acetamide derivatives:

Method A

To the stirred mixture of (3,4-dihydrospiro[chromene-2,1'-cyclobutan]-4-yl)acetic acid derivative (1.0 mmol) and arylamine hydrochloride (1.0 mmol) in dichloromethane was added 3-(3-dimethylaminopropyl)-1-ethylcarbodiimide hydrochloride (EDCI.HCl) (1.3 mmol), 1-hydroxybenzotriazole (HOBt) (1.3 mmol) and triethylamine (3.4 mmol). The reaction mixture was stirred at room temperature for 12 h. After the completion of the reaction, the reaction mixture was diluted with water and extracted with chloroform and the combined organic layers were washed with water, brine, dried (Na$_2$SO$_4$), filtered and concentrated under vacuum to yield the product.

Method B

Step 1

To the stirred solution of (3,4-dihydrospiro[chromene-2,1'-cyclobutan]-4-yl)acetic acid derivative (1.0 mmol) in dichloromethane was added oxalyl chloride (1.5 mmol) and catalytic amounts of N,N-dimethylformamide. The reaction mixture was stirred at room temperature for 2 h under nitrogen atmosphere. The solvent and excess of oxalyl chloride were evaporated under reduced pressure to give the acid chloride as sticky solid, which was used as such for coupling reaction without purification.

Step 2

To a stirred and cooled mixture of arylamine (1.0 mmol) and triethylamine (1.7 mmol) in dichloromethane was added the Step 1 intermediate (1.0 mmol) in dichloromethane over 15 min at 0° C. The reaction mixture was allowed to warm to room temperature and stirred at the same temperature under nitrogen for 2 h. The reaction mixture was diluted with water and the product was extracted with chloroform. The combined organic layers were washed with water, brine, dried (Na$_2$SO$_4$) filtered and concentrated under vacuum to yield the product.

Example 1

2-(6-Chloro-3,4-dihydrospiro[chromene-2,1'-cyclobutan]-4-yl)-N-(2-methoxyphenyl)acetamide

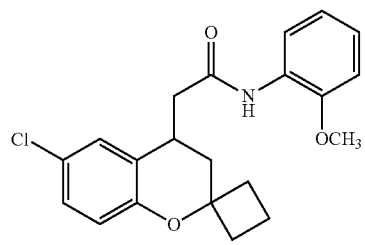 [SMILES: COc1ccccc1NC(=O)CC1CC2(CCC2)Oc2ccc(Cl)cc21]

The title compound was prepared by coupling 6-chloro-3,4-dihydrospiro[chromene-2,1'-cyclobutan]-4-yl)acetyl chloride (230 mg, 0.812 mmol), prepared from Intermediate 1, with 2-methoxyaniline (100 mg, 0.812 mmol) in presence of triethylamine (225 μl, 1.624 mmol) in dichloromethane (10 ml) as described in Method B to give 159 mg of the product as an off-white solid. IR (KBr) 3301, 2941, 1656, 1542, 1247, 1030, 742 cm$^{-1}$; $^1$H NMR (300 MHz, CDCl$_3$) δ 1.62-1.75 (m, 2H), 1.81-1.89 (m, 1H), 2.02-2.10 (m, 3H), 2.33-2.48 (m, 3H), 3.04 (dd, J=4.8, 9.6 Hz, 1H), 3.50 (br s, 1H), 3.81 (s, 3H), 6.72 (d, J=8.7 Hz, 1H), 6.85 (d, J=8.1 Hz, 1H), 6.93-7.04 (m, 3H), 7.14 (s, 1H), 7.75 (br s, 1H), 8.37 (d, J=6.9 Hz, 1H); ESI-MS (m/z) 372.25 (M+H)$^+$.

Example 2

2-(6-Chloro-3,4-dihydrospiro[chromene-2,1'-cyclobutan]-4-yl)-N-(2-cyclopentyloxy-3-methoxybenzyl)acetamide

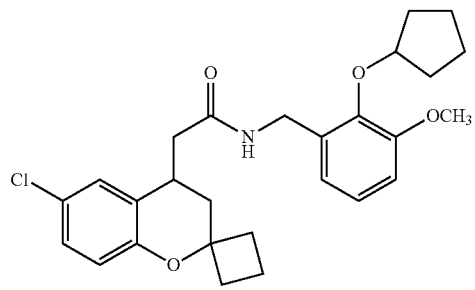 [SMILES: COc1cccc(CNC(=O)CC2CC3(CCC3)Oc3ccc(Cl)cc32)c1OC1CCCC1]

This title compound was prepared by coupling Intermediate 1 (207 mg, 0.828 mmol) with Intermediate 4 (200 mg, 0.828 mmol) in presence of EDCI.HCl (238 mg, 1.248 mmol), HOBt (190 mg, 1.242 mmol) and triethylamine (460 μl, 3.312 mmol) in dichloromethane (5 ml) as described in Method A to give 157 mg of the product as a white solid; IR (KBr) 3279, 2938, 1646, 1478, 1269, 1077 cm$^{-1}$; $^1$H NMR (300 MHz, CDCl$_3$) δ 1.50-1.67 (m, 5H), 1.81-2.06 (m, 6H), 2.09-2.19 (m, 4H), 2.28-2.39 (m, 1H), 2.75-2.82 (m, 1H), 3.40 (br s, 1H), 3.83 (s, 3H), 4.47 (d, J=6.0 Hz, 2H), 4.95 (br s, 1H), 6.03 (br s, 1H), 6.68 (d, J=8.7 Hz, 1H), 6.82-6.90 (m, 2H), 6.95-7.04 (m, 3H); ESI-MS (m/z) 468.46 (M−H)$^-$.

Example 3

2-(6-Chloro-3,4-dihydrospiro[chromene-2,1'-cyclobutan]-4-yl)-N-1-(4-methoxynaphthylmethyl)acetamide

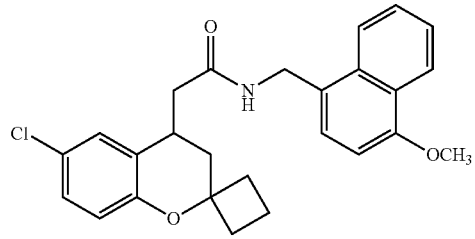 [SMILES: COc1ccc(CNC(=O)CC2CC3(CCC3)Oc3ccc(Cl)cc32)c2ccccc12]

The title compound was prepared by coupling Intermediate 1 (178 mg, 0.671 mmol) with Intermediate 5 (150 mg, 0.671 mmol) in presence of EDCI.HCl (192 mg, 1.008 mmol), HOBt (154 mg, 1.008 mmol) and triethylamine (375 μl, 2.686 mmol) in dichloromethane (5 ml) as described in Method A to give 103 mg of the product as a white solid; IR (KBr) 3289, 2933, 1632, 1480, 1092, 760 cm$^{-1}$; $^1$H NMR (300 MHz, CDCl$_3$) δ 1.42-1.68 (m, 5H), 1.80-1.85 (m, 1H), 2.03-2.16 (m, 3H), 2.74-2.81 (m, 1H), 3.44 (br s, 1H), 3.98 (s, 3H), 4.76-4.90 (m, 2H), 5.66 (br s, 1H), 6.65-6.73 (m, 2H), 6.96-7.04 (m, 2H), 7.33 (d, J=8.7 Hz, 1H), 7.46-7.55 (m, 2H), 7.92 (d, J=7.8 Hz, 1H), 8.28 (d, J=8.1 Hz, 1H); ESI-MS (m/z) 434.40 (M−H)$^-$.

Example 4

2-(6-Chloro-3,4-dihydrospiro[chromene-2,1'-cyclobutan]-4-yl)-N-[(4-methoxydibenzo[b,d]furan-1-yl)methyl]acetamide

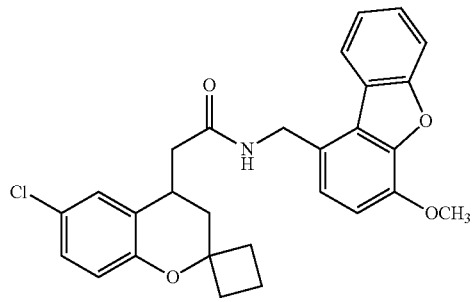 [SMILES: COc1ccc(CNC(=O)CC2CC3(CCC3)Oc3ccc(Cl)cc32)c2c1oc1ccccc12]

The title compound was prepared by coupling Intermediate 1 (121 mg, 0.455 mmol) with Intermediate 6 (100 mg, 0.379 mmol) in presence of EDCI.HCl (109 mg, 0.569 mmol), HOBt (87 mg, 0.569 mmol) and triethylamine (158 µl, 1.138 mmol) in dichloromethane (5 ml) as described in Method A to give 64 mg of the product as a white solid; IR (KBr) 3292, 2934, 1630, 1479, 1274, 747 cm$^{-1}$; $^1$H NMR (300 MHz, CDCl$_3$) δ 1.50-1.67 (m, 3H), 1.90-2.02 (m, 3H), 2.17-2.29 (m, 3H), 2.79 (dd, J=4.8, 9.6 Hz, 1H), 3.47 (br s, 1H), 4.05 (s, 3H), 4.83-4.98 (m, 2H), 5.68 (br s, 1H), 6.65 (d, J=8.1 Hz, 1H), 6.91-7.04 (m, 3H), 7.16 (d, J=7.8 Hz, 1H), 7.35 (t, J=7.2 Hz, 1H), 7.46 (d, J=7.8 Hz, 1H), 7.62 (d, J=8.4 Hz, 1H), 7.96 (d, J=7.8 Hz, 1H); ESI-MS (m/z) 475.90 (M)$^+$.

Example 5

2-(6-Chloro-3,4-dihydrospiro[chromene-2,1'-cyclobutan]-4-yl)-N-[(1S)-1-phenylethyl]acetamide

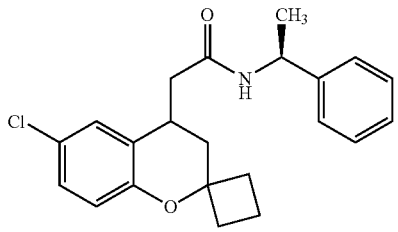 [SMILES: C[C@H](NC(=O)CC1CC2(CCC2)Oc2ccc(Cl)cc21)c1ccccc1]

The title compound was prepared by coupling acid chloride (117 mg, 0.412 mmol) of Intermediate 1 with (S)-(−)-α-methylbenzylamine (50 mg, 0.412 mmol) in dichloromethane (5 ml) in presence of triethylamine (172 µl, 1.238 mmol) as described in Method B to give 98 mg of the product as a white solid. $^1$H NMR (300 MHz, CDCl$_3$) δ 1.52-1.61 (m, 4H), 1.85 (br s, 1H), 1.98-2.05 (m, 4H), 2.27-2.38 (m, 3H), 2.72 (br s, 1H), 3.42 (br s, 1H), 5.17 (br s, 1H), 5.69 (br s, 1H), 6.70 (d, J=8.7 Hz, 1H), 7.00-7.09 (m, 2H), 7.31 (s, 5H).

Example 6

(2E)-2-(6-Chloro-3,4-dihydrospiro[chromene-2,1'-cyclobutan]-4-ylidene)-N-[2-(cyclopentyloxy)phenyl]acetamide

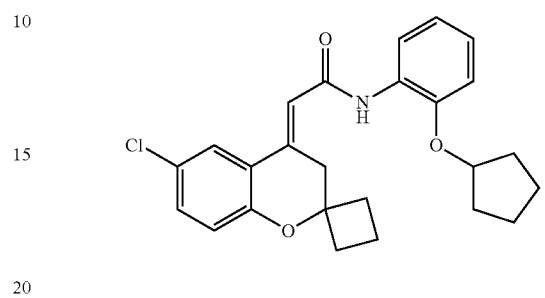

The title compound was prepared by the coupling ethyl (2E)-(6-chlorospiro[chromene-2,1'-cyclobutan]-4(3H)-ylidene)acetate (Step 2 of Intermediate 1) with 2-(cyclopentyloxy)aniline (120 mg, 0.681 mmol) (150 mg, 0.565 mmol) in presence of EDCI.HCl (163 mg, 0.851 mmol), HOBt (130 mg, 0.851 mmol) and triethylamine (157 µl, 1.134 mmol) in dichloromethane (5 ml) as described in Method A to give 95 mg of the product as a white solid; $^1$H NMR (300 MHz, CDCl$_3$) δ 1.53-1.65 (m, 8H), 1.74-1.90 (m, 4H), 2.22-2.30 (m, 2H), 2.47-2.57 (m, 2H), 3.50 (s, 2H), 4.67 (br s, 1H), 6.75 (d, J=8.1 Hz, 2H), 6.85-6.96 (m, 2H), 7.04-7.10 (m, 2H), 8.32 (d, J=7.8 Hz, 1H).

Example 7

N-(2-Cyclopentyloxyphenyl)-2-(6-fluoro-3,4-dihydrospiro[chromene-2,1'-cyclobutan]-4-yl)acetamide

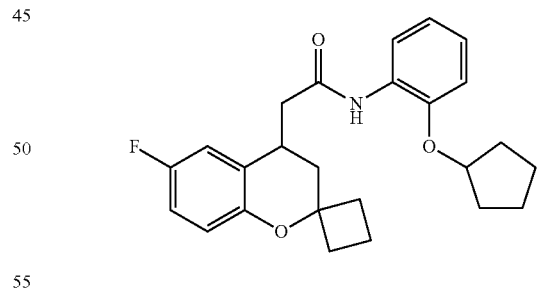

The title compound was prepared by coupling the acid chloride (121 mg, 0.451 mmol) of Intermediate 2 with 2-(cyclopentyloxy) aniline (80 mg, 0.451 mmol) in presence of triethylamine (188 µl, 1.353 mmol) in dichloromethane (5 ml) as described in Method B to give 89 mg of the product as a white solid; $^1$H NMR (300 MHz, CDCl$_3$) δ 1.53-1.60 (m, 1H), 1.64-1.75 (m, 6H), 1.81-1.90 (m, 4H), 1.92-2.07 (m, 3H), 2.30-2.42 (m, 3H), 3.02 (dd, J=4.8, 9.6 Hz, 1H), 3.52 (br s, 1H), 4.81 (br s, 1H), 6.74-6.81 (m, 2H), 6.87-7.04 (m, 4H), 7.76 (br s, 1H), 8.36 (d, J=8.1 Hz, 1H).

Example 8

N-(2,6-Difluorobenzyl)-2-(6-fluoro-3,4-dihydrospiro[chromene-2,1'-cyclobutan]-4-yl)acetamide

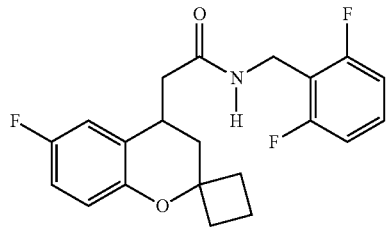 [SMILES: O=C(CC1CC2(CCC2)Oc2ccc(F)cc21)NCc1c(F)cccc1F]

The title compound was prepared by coupling the acid chloride (250 mg, 0.931 mmol) of Intermediate 2 with 2,6-difluorobenzylamine (133 µl, 1.117 mmol) in presence of triethylamine (388 µl, 2.793 mmol) in dichloromethane (5 ml) as described in Method B to give 219 mg of the product as a white solid; $^1$H NMR (300 MHz, CDCl$_3$) δ 1.58-1.70 (m, 3H), 1.79-1.89 (m, 1H), 2.00-2.07 (m, 2H), 2.16-2.21 (m, 2H), 2.29-2.39 (m, 1H), 2.75 (q, J=5.1 Hz, 1H), 3.43 (br s, 1H), 4.51-4.66 (m, 2H), 6.66-6.77 (m, 3H), 6.89 (t, J=7.8 Hz, 2H), 7.19-7.29 (m, 1H).

Example 9

2-(6-Fluoro-3,4-dihydrospiro[chromene-2,1'-cyclobutan]-4-yl)-N-quinolin-6-ylacetamide

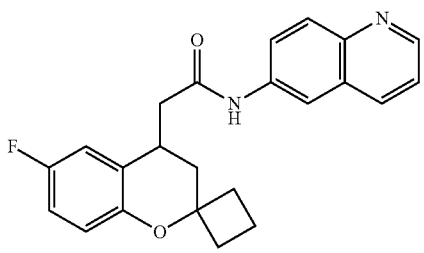 [SMILES: O=C(CC1CC2(CCC2)Oc2ccc(F)cc21)Nc1ccc2ncccc2c1]

The title compound was prepared by coupling the acid chloride (110 mg, 0.409 mmol) of Intermediate 2 with 6-aminoquinoline (65 mg, 0.451 mmol) in the presence of triethylamine (171 µl, 1.229 mmol) in dichloromethane (5 ml) as described in Method B to give 99 mg of the product as a white solid; $^1$H NMR (300 MHz, CDCl$_3$) δ 1.64-1.70 (m, 3H), 1.75-1.88 (m, 1H), 2.06-2.12 (m, 2H), 2.37-2.42 (m, 2H), 2.50-2.55 (m, 1H), 3.04 (dd, J=4.8, 10.2 Hz, 1H), 3.57 (br s, 1H), 6.77-6.89 (m, 3H), 7.37-7.42 (m, 1H), 7.50 (d, J=8.1 Hz, 1H), 7.76 (s, 1H), 8.07 (dd, J=7.8, 10.2 Hz, 2H), 8.40 (s, 1H), 8.82 (s, 1H).

Example 10

N-[4-(4-Bromophenyl)-1,3-thiazol-2-yl]-2-(6-fluoro-3,4-dihydrospiro[chromene-2,1'-cyclobutan]-4-yl)acetamide

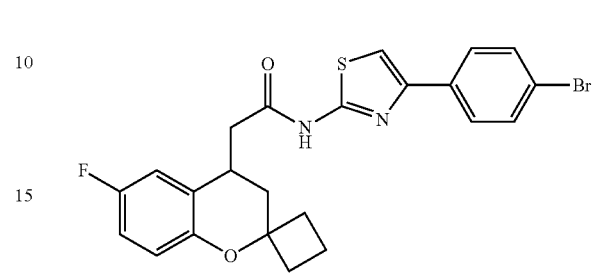

To a stirred solution of Intermediate 2 (100 mg, 0.399 mmol) in dimethylformamide (5 ml) was added 4-(4-bromophenyl)-1,3-thiazol-2-amine (122 mg, 0.679 mmol) followed by dicyclohexyl carbodimide (122 mg, 0.598 mmol) and N-hydroxysuccinimide (67 mg, 0.598 mmol). The reaction mixture was heated to 80° C. under nitrogen for 24 h. The reaction mixture was cooled to room temperature and the residue was filtered through a celite bed. The product was extracted with ethyl acetate (3×50 ml) and the combined organic layers were washed by water, brine and dried (Na$_2$SO$_4$). The crude product obtained after evaporation under reduced pressure was purified by silica gel column chromatography using 5% ethyl acetate in petroleum ether to give 79 mg of the product as an off-white solid; $^1$H NMR (300 MHz, CDCl$_3$) δ 1.45-1.55 (m, 2H), 1.58-1.70 (m, 2H), 1.84-1.90 (m, 1H), 1.98-2.10 (m, 2H), 2.16-2.22 (m, 1H), 2.31-2.38 (m, 1H), 2.77 (dd, J=4.2, 10.8 Hz, 1H), 3.40 (br s, 1H), 6.56 (d, J=8.7 Hz, 1H), 6.72-6.79 (m, 2H), 7.13 (s, 1H), 7.47 (d, J=8.1 Hz, 2H), 7.60 (d, J=8.4 Hz, 2H), 10.42 (br s, 1H).

Example 11

2-(6-Methoxy-3,4-dihydrospiro[chromene-2,1'-cyclobutan]-4-yl)-N-1-naphthylacetamide

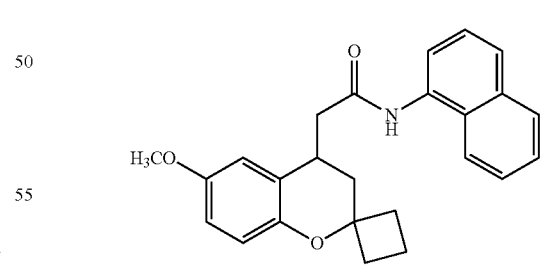

The title compound was prepared by coupling the acid chloride (195 mg, 0.698 mmol) of Intermediate 3 with 1-aminonaphthalene (100 mg, 0.698 mmol) in the presence of triethylamine (291 µl, 2.095 mmol) in dichloromethane (5 ml) as described in Method B to give 128 mg of the product as a white solid; $^1$H NMR (300 MHz, CDCl$_3$) δ 1.63-1.70 (m, 2H), 1.76-1.84 (m, 2H), 2.03-2.10 (m, 3H), 2.34-2.40 (m, 2H), 2.73-2.80 (m, 1H), 3.09 (q, J=4.8 Hz, 1H), 3.60 (br s, 1H), 3.72 (s, 3H), 6.73-6.82 (m, 2H), 7.45-7.52 (m, 5H), 7.66 (d, J=8.1 Hz, 1H), 7.82 (d, J=7.5 Hz, 1H), 7.96 (d, J=7.2 Hz, 1H).

Example 12

2-(6-Methoxy-3,4-dihydrospiro[chromene-2,1'-cyclobutan]-4-yl)-N-1,3-thiazol-2-ylacetamide

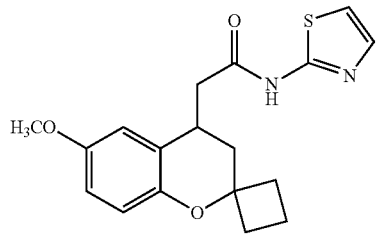 [SMILES: COc1ccc2c(c1)C(CC(=O)Nc1nccs1)CC1(CCC1)O2]

The title compound was prepared by coupling the acid chloride (100 mg, 0.356 mmol) of Intermediate 3 with 2-amino-1,3-thiazole (35 mg, 0.356 mmol) in the presence of triethylamine (149 µl, 1.068 mmol) in dichloromethane (5 ml) as described in Method B to give 85 mg of the product as a white solid; $^1$H NMR (300 MHz, CDCl$_3$) δ 1.62-1.71 (m, 2H), 1.88 (br s, 1H), 2.05-2.12 (m, 3H), 2.30-2.41 (m, 2H), 2.59-2.67 (m, 1H), 3.19 (q, J=4.8 Hz, 1H), 3.58 (br s, 1H), 3.69 (s, 3H), 6.68-6.75 (m, 3H), 6.93-6.70 (m, 1H), 7.28-7.35 (m, 1H).

Example 13

2-(6-Methoxy-3,4-dihydrospiro[chromene-2,1'-cyclobutan]-4-yl)-N-(6-Methyl-1,3-benzothiazol-2-yl)acetamide

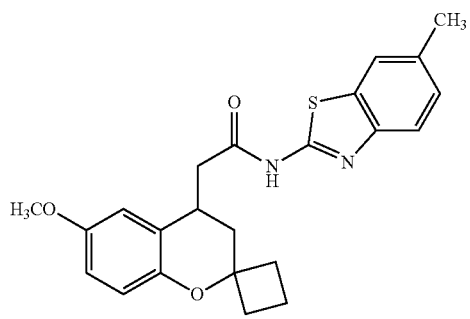 [SMILES: COc1ccc2c(c1)C(CC(=O)Nc1nc3ccc(C)cc3s1)CC1(CCC1)O2]

The title compound was prepared by coupling the acid chloride (170 mg, 0.608 mmol) of Intermediate 3 with 6-methyl-1,3-benzothiazol-2-amine (100 mg, 0.608 mmol) in the presence of triethylamine (254 µl, 1.826 mmol) in dichloromethane (5 ml) as described in Method B to give 80 mg of the product as a white solid; $^1$H NMR (300 MHz, CDCl$_3$) δ 1.60-1.68 (m, 3H), 1.86 (br s, 1H), 1.98-2.05 (m, 3H), 2.28-2.35 (m, 2H), 2.46 (s, 3H), 2.55-2.60 (m, 1H), 3.10 (q, J=4.8 Hz, 1H), 3.55 (br s, 1H), 3.66 (s, 3H), 6.61 (br s, 1H), 6.69-7.77 (m, 2H), 7.17 (d, J=7.8 Hz, 1H), 7.53-7.60 (m, 2H). ESI-MS (m/z) 409.43 (M+H)$^+$.

Pharmacological Activity

The illustrative examples of the present invention are screened for TRPV3 activity according to a modified procedure described in Tóth, A., Kedei, N., Wang, Y. and Blumberg, P. M. *Life Sciences* (2003), 73, 487-498. The screening of the compounds can be carried out by other methods and procedures known to a person skilled in the art. Such screening methods may be found in (a) Hu, H.-Z. et al. *J. Biol. Chem.* (2004), 279, 35741-35747; (b) Smith, G. D. et al. *Nature* (2002), 418, 186-190; (c) Peier, A. M. et al. *Science* (2002), 296, 2046-2049.

Screening for TRPV3 Antagonist Using the $^{45}$Calcium Uptake Assay:

The inhibition of TRPV3 receptor activation was followed as inhibition of 2-aminoethoxydiphenylborate (2-APB) induced cellular uptake of radioactive calcium. Test compounds were dissolved in dimethyl sulfoxide (DMSO) to prepare 20 mM stock solution and then diluted using plain medium with DMEM/F-12 containing 1.8 mM CaCl$_2$ to get desired concentration. Final concentration of DMSO in the reaction was 0.5% (v/v). Human TRPV3 expressing CHO cells were grown in DMEM/F-12 medium with 10% FBS, 1% penicillin-streptomycin solution, 400 µg/ml of G-418. Cells were seeded 24 h prior to the assay in 96 well plates so as to get ~50,000 cells per well on the day of experiment. Cells were treated with test compounds for 10 minutes followed by addition of 2-APB at a final concentration of 500 µM and 5 µCi/ml$^{45}$Ca$^{+2}$ for 4 minutes. Cells were washed and lysed using buffer containing 1% Triton X-100, 0.1% deoxycholate and 0.1% SDS. Radioactivity in the lysate was measured in Packardt Top count after addition of liquid scintillant. Concentration response curves were plotted as a % of maximal response obtained in the absence of test antagonist. IC$_{50}$ value was calculated from concentration response curve by nonlinear regression analysis using GraphPad PRISM software.

The compounds prepared were tested using the above assay procedure and the results obtained are given in Table 1. Percentage inhibition at concentrations of 1.0 µM and 10.0 µM are given in the table-1.

TABLE 1

In-vitro screening results of compounds of invention:

| Example | Percentage inhibition | | IC$_{50}$ n.M |
|---|---|---|---|
| | at 1.0 µM | at 10.0 µM | |
| Example 1 | 26.3 | 94.2 | — |
| Example 2 | 61.6 | 92.9 | 725.3 |
| Example 3 | 54.6 | 83.9 | — |
| Example 4 | 23.2 | 52.3 | — |
| Example 5 | 6.3 | 65.8 | — |
| Example 6 | 51.5 | 80.9 | — |
| Example 7 | 46.8 | 93.8 | — |
| Example 8 | 14.2 | 53.1 | — |
| Example 9 | 3.7 | 88.5 | — |
| Example 10 | 49.3 | 77.9 | — |
| Example 11 | 29.1 | 86.5 | — |
| Example 12 | 19.4 | 63.6 | — |
| Example 13 | 26.1 | 66.8 | — |

The invention claimed is:
1. A compound of the formula (I):

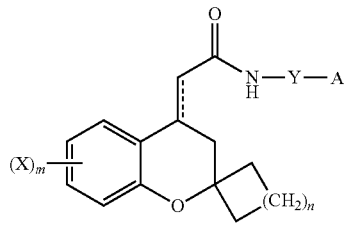

wherein dotted ( . . . ) line is absent;
A is substituted or unsubstituted cycloalkyl, aryl, heteroaryl, or heterocyclic group;
Y is —(CHR$^1$)$_r$ wherein R$^1$ is hydrogen, halogen, or substituted or unsubstituted alkyl;
X is hydrogen, nitro, cyano, halogen, substituted or unsubstituted alkyl, —OR$^2$, —NR$^3$R$^4$, —C(O)—R$^3$, —C(O)O—R$^3$, —C(O)NR$^3$R$^4$, —S(O)$_p$NR$^3$R$^4$, or —S(O)$_p$R$^3$;
at each occurrence R$^3$ and R$^4$, which may be same or different, are independently selected from hydrogen, —OR$^2$, substituted or unsubstituted alkyl, alkenyl, cycloalkyl cycloalkylalkyl, cycloalkenyl, aryl, arylalkyl, heteroaryl, heteroarylalkyl, heterocyclic group, or heterocyclylalkyl;
at each occurrence R$^2$ is selected from the group consisting of hydrogen, substituted or unsubstituted alkyl, alkenyl, cycloalkyl, aryl, heteroaryl, heterocyclic group, cycloalkylalkyl, arylalkyl, heteroarylalkyl, or heterocyclylalkyl;
'm' is an integer ranging from 0 to 2, both inclusive;
'n' is an integer ranging from 0 to 2, both inclusive;
'p' is an integer ranging from 0 to 2, both inclusive; and
'r' is an integer ranging from 0 to 2, both inclusive;
or pharmaceutically acceptable salts thereof.

2. The compound according to claim 1, wherein Y is —(CHR$^1$)$_r$ where 'r' is 0 or 1.

3. The compound according to claim 2, wherein R$^1$ is hydrogen or substituted or unsubstituted alkyl.

4. The compound according to claim 1 wherein A is substituted or unsubstituted aryl.

5. The compound according to claim 1, wherein A is substituted or unsubstituted heteroaryl.

6. The compound according to claim 1, wherein 'n' is 1.

7. The compound according to claim 1, selected from
2-(6-Chloro-3,4-dihydrospiro[chromene-2,1'-cyclobutan]-4-yl)-N-(2-methoxyphenyl)acetamide,
2-(6-Chloro-3,4-dihydrospiro[chromene-2,1'-cyclobutan]-4-yl)-N-(2-cyclopentyloxy-3-methoxy benzyl)acetamide,
2-(6-Chloro-3,4-dihydrospiro[chromene-2,1'-cyclobutan]-4-yl)-N-1-(4-methoxynaphthylmethyl)acetamide,
2-(6-Chloro-3,4-dihydrospiro[chromene-2,1'-cyclobutan]-4-yl)-N-[(4-methoxydibenzo[b,d]furan-1-yl)methyl]acetamide,
2-(6-Chloro-3,4-dihydrospiro[chromene-2,1'-cyclobutan]-4-yl)-N-[(1S)-1-phenylethyl]acetamide,
N-(2-Cyclopentyloxyphenyl)-2-(6-fluoro-3,4-dihydrospiro[chromene-2,1'-cyclobutan]-4-yl)acetamide,
N-(2,6-Difluorobenzyl)-2-(6-fluoro-3,4-dihydrospiro[chromene-2,1'-cyclobutan]-4-yl)acetamide,
2-(6-Fluoro-3,4-dihydrospiro[chromene-2,1'-cyclobutan]-4-yl)-N-quinolin-6-ylacetamide,
N-[4-(4-Bromophenyl)-1,3-thiazol-2-yl]-2-(6-fluoro-3,4-dihydrospiro[chromene-2,1'-cyclobutan]-4-yl)acetamide,
2-(6-Methoxy-3,4-dihydrospiro[chromene-2,1'-cyclobutan]-4-yl)-N-1-naphthylacetamide,
2-(6-Methoxy-3,4-dihydrospiro[chromene-2,1'-cyclobutan]-4-yl)-N-1,3-thiazol-2-ylacetamide, and
2-(6-Methoxy-3,4-dihydrospiro[chromene-2,1'-cyclobutan]-4-yl)-N-(6-Methyl-1,3-benzothiazol-2-yl)acetamide or
pharmaceutically acceptable salts thereof.

8. A pharmaceutical composition comprising a compound according to claim 1, either as a free base or pharmaceutically acceptable salt form and a pharmaceutically acceptable excipient.

9. The pharmaceutical composition according to claim 8, wherein the pharmaceutically acceptable excipient is a carrier or diluent.

10. A method for treating a vanilloid receptor mediated disease, disorder or syndrome in a subject in need thereof comprising administering to the subject a therapeutically effective amount of a compound according to claim 1.

11. The method according to claim 10, wherein the vanilloid receptor is TRPV3.

12. The method according to claim 11, wherein the symptoms of a disease, disorder, syndrome or condition associated with TRPV3 function is selected from the group consisting of pain, acute pain, chronic pain, nociceptive pain, neuropathic pain, post-operative pain, dental pain, cancer pain, cardiac pain arising from an ischemic myocardium, pain due to migraine, arthralgia, neuropathies, neuralgia, trigeminal neuralgia nerve injury, diabetic neuropathy, neurodegeneration, retinopathy, neurotic skin disorder, stroke, urinary bladder hypersensitiveness, urinary incontinence, vulvodynia, gastrointestinal disorders such as irritable bowel syndrome, gastro-esophageal reflux disease, enteritis, ileitis, stomach-duodenal ulcer, inflammatory bowel disease, Crohn's disease, celiac disease, an inflammatory disease such as pancreatitis, a respiratory disorder such as allergic and non-allergic rhinitis, asthma or chronic obstructive pulmonary disease, irritation of skin, eye or mucous membrane, dermatitis, pruritic conditions such as uremic pruritus, fervescence, muscle spasms, emesis, dyskinesias, depression, Huntington's disease, memory deficits, restricted brain function, amyotrophic lateral sclerosis (ALS), dementia, arthritis, osteoarthritis, diabetes, obesity, urticaria, actinic keratosis, keratocanthoma, alopecia, Meniere's disease, tinnitus, hyperacusis, anxiety disorders and benign prostate hyperplasia.

13. A method of treating pain in a subject in need thereof comprising administering to the subject a therapeutically effective amount of a compound of claim 1.

14. The method according to claim 13, wherein the pain is acute pain.

15. The method according to claim 13, wherein the pain is chronic pain.

16. The method according to claim 13, wherein the pain is post-operative pain.

17. A method of treating neuropathic pain in a subject in need thereof comprising administering to the subject a therapeutically effective amount of a compound of claim 1.

18. A method of treating inflammation in a subject in need thereof comprising administering to the subject a therapeutically effective amount of a compound of claim 1.

19. The method according to claim 13, wherein the pain is neuropathic pain.

* * * * *